(12) United States Patent
Bertora et al.

(10) Patent No.: US 11,446,492 B2
(45) Date of Patent: Sep. 20, 2022

(54) ELECTRICAL STIMULATION APPARATUS

(71) Applicant: Fremslife S.r.l., Genoa (IT)

(72) Inventors: Franco Bertora, Genoa (IT); Michele Palermo, Genoa (IT)

( * ) Notice: Subject to any disclaimer, the term of this patent is extended or adjusted under 35 U.S.C. 154(b) by 0 days.

(21) Appl. No.: 15/733,501

(22) PCT Filed: Feb. 27, 2019

(86) PCT No.: PCT/IB2019/051572
§ 371 (c)(1),
(2) Date: Aug. 13, 2020

(87) PCT Pub. No.: WO2019/166965
PCT Pub. Date: Sep. 6, 2019

(65) Prior Publication Data
US 2021/0101004 A1    Apr. 8, 2021

(30) Foreign Application Priority Data

Feb. 27, 2018 (IT) .......... 102018000003075

(51) Int. Cl.
*A61N 1/36* (2006.01)
*A61N 1/04* (2006.01)

(52) U.S. Cl.
CPC ......... *A61N 1/3603* (2017.08); *A61N 1/0452* (2013.01); *A61N 1/0456* (2013.01); *A61N 1/0476* (2013.01); *A61N 1/0484* (2013.01)

(58) Field of Classification Search
CPC .. A61N 1/3603; A61N 1/0452; A61N 1/0456; A61N 1/0476; A61N 1/0484;
(Continued)

(56) References Cited

U.S. PATENT DOCUMENTS

2009/0264809 A1* 10/2009 Sen ............... A61K 48/0075
604/20
2013/0085317 A1* 4/2013 Feinstein ........... A61N 1/36021
600/14
(Continued)

FOREIGN PATENT DOCUMENTS

WO          0102052       1/2001
WO          2007107831    9/2007
WO          2016113661    7/2016

*Primary Examiner* — Carl H Layno
*Assistant Examiner* — Anh-Khoa N Dinh
(74) *Attorney, Agent, or Firm* — Themis Law

(57) ABSTRACT

An electrical stimulation apparatus includes a generator of sequential electrical pulses having predetermined values of parameters that include pulse amplitude, and duration and frequency of the pulses, the generator having one or more separate stimulation channels that independently deliver the pulse sequences to body areas. An electrode for each channel transmits the stimulation pulses and is applied outside the patient's skin at a predetermined region and with a predetermined position relative to the position of another electrode associated to another channel. One or more electrodes are borne by a flexible support element, fastenable in a position related to body anatomy, and are distributed on an extension of the support element according to a predetermined design, together with the pulse generator connected to the one or more electrodes or with two or more pulse generators connected to different electrodes also supported by the support element.

20 Claims, 10 Drawing Sheets

(58) Field of Classification Search
CPC .... A61N 1/0488; A61N 1/048; A61N 1/0492; A61N 1/0496; A61N 2001/083; A61N 1/086; A61N 1/08; A61N 1/10; A61N 1/18; A61N 1/20; A61N 1/22; A61N 1/24; A61N 1/26; A61N 1/28; A61N 1/30
See application file for complete search history.

(56) References Cited

U.S. PATENT DOCUMENTS

2015/0306373 A1\* 10/2015 Bouton .............. A61N 1/36003
607/48
2016/0114160 A1\* 4/2016 Scott .................... A61N 1/0452
607/46

\* cited by examiner

ELECTRICAL STIMULATION APPARATUS

FIELD OF THE INVENTION

The present invention concerns an electrical stimulation apparatus, comprising
at least one generator of electrical pulses, which pulses are arranged in sequences having predetermined values of typical parameters, said typical parameters comprising amplitude, duration and frequency of said pulses;
said generator comprising one or more separate stimulation channels, such to deliver said sequences to body areas of an organism in a manner independent for each channel;
at least one stimulation electrode for each stimulation channel and each of them transmits the stimulation pulses of a corresponding channel;
each electrode is applied outside the patient skin at a predetermined region and with a predetermined position relation with respect to the position of one or more further electrodes associated to each of the further channels of said plurality of channels;
a control unit of said at least one electrical pulse generator, communicating with said electrical pulse generator;
an interface for entering setting data and/or commands and for displaying setting data and/or configuration settings of said one or more generators.

BACKGROUND OF THE INVENTION

Clinical data shows that electrical stimulation brings benefits in many pathological conditions, such as for example in the treatment of ulcers, sores or lesions, in the treatment of pain, in the treatment of obesity and also in the vascular setting.

For example, more than half of the population of Western countries suffers from diseases related to the vascular setting, in particular to the cardiovascular system. Alterations caused by degenerative diseases such as arteriosclerosis frequently manifest themselves in the vascular walls, which, together with thrombosis, is one of the most frequent causes of obstruction of the peripheral arteries and of those involving the myocardium and brain.

Arteriosclerosis manifests itself in a particularly aggressive and premature way in diabetic patients, which are about 3% of the population in Europe and similar percentages of the population in Italy. This disease is accompanied by highly debilitating long-term complications for the patient, due to the degeneration of the major vessels (macro-angiopathy), of the small vessels (micro-angiopathy) and the peripheral and vegetative (neuropathy) nervous system. In diabetic patients, peripheral macro-angiopathy generates symptoms similar to those observed in non-diabetic patients; however, it manifests itself prematurely and with greater frequency, and worsens rather rapidly.

As a result of the above-mentioned reasons, in diabetic patients, vascular diseases determine a double mortality with respect to non-diabetic patients and require long term hospitalizations, with heavy economic and social consequences.

Moreover, in diabetic patients, arteriosclerosis is responsible for most of the lower limb amputations (50-70%), which manifest themselves in these patients with a frequency 5 times higher than in non-diabetic patients. The occlusion of the distal arteries of small and medium bore below the knee is responsible for the development of gangrene. Furthermore, diabetic patients are more frequently suffering from claudicatio intermittens due to calf, thigh or buttock muscle ischemia, than the non-diabetic ones.

Some substances produced from endothelial cells, which cause the formation of new blood vessels (angiogenesis) and vasodilation, such as for example the Fibroblast Growth Factor (FGF), the Neural Growth Factor (NGF), the Vascular Endothelial Growth Factor (VEGF), were recently discovered and described in literature.

VEGFs and other angiogenic factors, such as FGFs, can be directly injected into the vascular bed affected by ischemia and/or occlusion to promote angiogenesis. However, the direct injection of VEGFs or other angiogenic factors involves numerous drawbacks, mainly due to the release difficulties with regards to all the cells affected. In fact, less than 2% of VEGFs injected effectively participates in the neo-angiogenesis; moreover, the method is potentially toxic.

Experiments conducted by Kanno et al. demonstrated that by applying continuous electrical stimulation for 5 days onto isolated animal muscles, by means of pulses having an amplitude of 0.3 ms, a frequency of 50 Hz and an intensity of 0.1 V, an increase in the production of VEGFs is observed and neo-angiogenesis is promoted, through an increase in the number of capillaries and blood flow.

Although these experiments appear to suggest that the electrical stimulation of muscles has beneficial effects on circulation, they do not explain how to apply electrical stimulation to human beings.

Moreover, they require a treatment time of several days, which could cause discomfort to the patient due to its excessive length.

Moreover, it is known to use laser transmyocardial revascularization to reduce the pain caused by angina; this determines an increase in the level of VEGFs in the myocardium and in the endothelial cells of capillaries and arterioles ((Lee, S H, Wolf P L, Escudero R, N Eng. J. Med. 2000; 342, 626-33). However, laser transmyocardial revascularization is an invasive technique which leads to limited results.

US 2002/0010492 describes an electrical stimulation device for the controlled production of angiogenic growth factors, through which it is possible, in vitro, to increase the level of VEGFs by 30-40% with a continuous electrical stimulation of a duration of at least 8 hours.

Also in this case, however, long treatment times are required which cause significant discomforts for the patient.

WO 02/09809 describes an apparatus for the treatment of vascular, or muscular, or tendon diseases, by which a series of electrical pulses having an amplitude of 10 to 40 μs and an intensity of 100 to 170 μA is applied to a patient. This way, it is possible to achieve an increase in the production of VEGFs, with consequent vasodilation and neo-angiogenesis.

WO 2004/084988 describes an electrical stimulation apparatus thanks to which, depending on the type of electrical stimulation generated and on the configuration settings adopted, it is possible to generate a neuro-induced bioactive modulation, apt to produce phenomena of the vasoactive type on microcirculation and macrocirculation.

In turn, these phenomena are mediated by phenomena connected to the direct stimulation of smooth muscles and by phenomena essentially of the catecholaminergic type, through the stimulation of post-synaptic receptors. The aforesaid apparatus is able to generate specific stimulation sequences which induce reproducible and constant neurophysiological responses.

In particular, WO 2004/084988 describes an activation sequence of microcirculation (ATMC) and a decontracting sequence of muscular fibers (DCTR), which are able to stimulate different functional contingents, among which the striated muscle, the smooth muscle and the mixed peripheral nerve. The aforesaid stimulation sequences are assembled on three essential parameters: the duration of the stimulus, the frequency of the stimulus and the time intervals during which different duration/frequency combinations follow one another. The general operating model of the stimulation sequences reflects the digital-analogue transduction which occurs in the transmission of a nervous pulse.

The frequency and amplitude modulated neuronal electrical stimulation or FREMS~(Frequency Rhythmic Electric Modulation described in the aforesaid WO 2004/084988 and in WO 2004/067087, herein incorporated for reference), is characterized by the use of transdermal electric currents, produced by sequential electrical pulses of variable frequency and duration. The frequency can vary from 0.1 to 999 Hz, the duration of the stimulus is between 0.1 and 40 µs and the voltage, maintained constant above the perceptive threshold, is between 0.1 and 300 V (preferably 150 V). By appropriately combining the aforesaid variations in frequency and duration, a specific sequence is obtained, defined DCTR, having a decontracting effect and comprising a series of substeps, named A, B and C. Frequency and amplitude are constant in the substep A, the frequency is constant and the amplitude variable in the substep B, the frequency is variable and the amplitude constant in the substep C.

Experimental studies allowed to assess the effects of FREMS and the ability of the latter to evoke compound muscle action potentials (cMAP) achievable in the adductor muscle of the big toe by stimulating the posterior tibial nerve, as well as the amplitude variation of the H reflex by using the latter as a conditioning stimulus. As described in WO 2004/084988, the aforesaid experimental studies also demonstrated that the greatest amplitude of cMAPs (0.60±0.02 mV) achievable is about 15 times less than that of the cMAPs achievable with known devices delivering TENS currents, i.e. amplitudes in the order of 9±0.6 mV with stimuli having a duration typically included in a range of 200-1000 µs. It was also observed that the maximum amplitude value of the cMAPs is achieved in the presence of a duration/frequency ratio equal to 0.13 (40 µs/29 Hz).

A further type of sequence, named ATCM and suitably designed to achieve a vasoactive effect, has a prevailing action on the motility of microcirculation, i.e. of the smooth sphincters of the arterioles and venules of subcutaneous tissue. In practice, as described in WO 2004/084988, a system which generates a sequence of vasodilations and vasoconstrictions with sequential increases and decreases in the blood flow of the micro-circulation surrounding the stimulation region is achieved. These vasodilations and vasoconstrictions generate a "pump" effect clearly produced by a neuromodulation of the sympathetic neurovegetative system, which influences vasoaction just through the smooth musculature of the capillary vessels and arterioles. This way, it can be highlighted that such subsequence, characterized by alternate rheobase variations, therefore generates a vasoactive effect consisting of sequential vasodilation steps and vasoconstriction steps. This certainly also generates a draining effect and, especially, an elasticization of microcirculation and a modulation of the latter around a main leading event which determines its average variation.

Studies also demonstrated how electrical stimulation can promote the transdermal absorption of drugs and therefore increase the efficacy thereof.

The electrical stimulation sessions generally require relatively long times and the current devices are made so that to require a patient to remain essentially still or in a resting condition, preventing him from moving and the posture variations which require movements of a certain extent.

In these devices, the relative electronic circuits of the user interface, the control unit and the pulse generators are integrated in a single casing, generally in the form of a stationary and relatively bulky device, of the table type, while each electrode is associated to the body of the patient by means of removable fastening means at a predetermined point and is connected at the output of a corresponding channel which is provided on said casing by means of a cable for transmitting the pulses emitted by said channel.

The document US2013/0085317 shows a device for the treatment of musculoskeletal disorders. The device comprises a rigid supporting structure in the form of a knee-high, which knee-high consists of a flat element which is wound around the leg and is fastened in position by means of tightening against the leg thanks to tightening straps.

The knee-high has a plurality of electrodes and relative connections to a central electrical pulse control and supply device, which pulses must be supplied to the limb through the electrodes.

The knee-high therefore constitutes a relatively rigid tutor-like structure or the like. Moreover, the application is of the musculoskeletal type and neither vascular, nor neurological.

Therefore, despite the efficacy of the electrical stimulation treatment with additional treatment and of an increase in the therapeutic effects in the different aforesaid diseases and in other further diseases still currently under study, for the practical aforesaid reasons, and therefore for the duration of the single sessions and number of sessions over time, i.e. the overall length of the treatments especially in case of chronic diseases, the electrical stimulation apparatuses and the treatments carried out with them make patients unwilling to use them or the treatments are interrupted when the first benefits arise, therefore compromising the achievement of a condition of complete recovery or of a reduction of the symptoms of the disease below given threshold conditions.

SUMMARY OF THE INVENTION

An aspect of the invention consists in perfecting the currently available apparatuses, overcoming the limitations of the current apparatuses as far as the comfort and practicality of use is concerned and extending the usability of the treatments in any condition of the patient during the normal course of daily activities, so that to make the therapeutic treatment possible in a continuous way or for long treatment times without compromising the mobility of the patient.

A further aspect of the invention consists in perfecting an apparatus of the aforesaid type so that to make the configuration of an electrical stimulation apparatus, with respect to a particular and specific application and/or the modification of the electrical stimulation apparatus for a progressive adaptation to the health conditions in course of a treatment which includes a number of treatment sessions spread over a long period of time, extremely easy and quick.

Still a further aspect of the present invention is to improve the electrical stimulation apparatus so that to be able to use it in combination with other types of treatments, such as for example those of transdermal drug intake and/or localized heat treatments.

With regard to the above, an aspect of the present invention provides to improve the electrical stimulation apparatus so that to be able to have the maximum flexibility possible with respect to the various medical devices for the administration of drugs by transdermal absorption and to be able to couple the electrical stimulation apparatus with pre-existing pharmacological devices.

The invention achieves the aforesaid objects with an electrical stimulation apparatus, comprising at least one generator of electrical pulses, which pulses are arranged in sequences having predetermined values of typical parameters, said typical parameters comprising amplitude, duration and frequency of said pulses;

said generator comprising one or more separate stimulation channels, such to deliver said sequences to body areas of an organism in a manner independent for each channel;

at least one stimulation electrode for each stimulation channel and each of them transmits the stimulation pulses of a corresponding channel;

each electrode is applied outside the patient skin at a predetermined region and with a predetermined position relation with respect to the position of one or more further electrodes associated to each of the further channels of said plurality of channels;

a control unit of said at least one electrical pulse generator, communicating with said electrical pulse generator;

an interface for entering setting data and/or commands and for displaying setting data and/or configuration settings of said one or more generators, and wherein said at least one electrode or a given number of electrodes is supported by a self-adhesive flexible support element, which is fastenable in a predetermined position in relation to the anatomy of the human body;

said electrodes being distributed on the extension of said self-adhesive flexible support element according to a predetermined design that is determined by predetermined relations of the space positions of the individual electrodes one with respect to each other;

the at least one pulse generator being connected to the at least one electrode and/or the plurality of electrodes provided on the flexible support element or two or more pulse generators connected to different one or more electrodes of said plurality of electrodes, the latter being supported also by said flexible support element, while said one or more pulse generators being provided with a communication unit for each of them or shared by at least part of each of them, which communication unit is connected to the communication unit of at least one control unit of said one or more generators.

As will become clear in a more detailed way also from the following description, it is possible to provide different configurations which allow to adapt the electrical stimulation apparatus to different levels of portability, comfort and ease of use which can be selected from time to time depending on the therapeutic applications and treatment protocols provided for the specific cases and which require different cost and evolutionary levels of the apparatus.

A first embodiment provides that a flexible support is provided with one or more electrodes and a pulse generator shared by said electrodes, each of which is connected to a dedicated independent channel transmitting the stimulation pulses to the corresponding electrode.

According to a variant of this embodiment, the control unit that controls said generator is directly associated to the generator and is provided with it on a shared support, such as for example on the same flexible support of the electrodes or on a dedicated flexible support.

According to a further variant, the control unit is separated from the generator and is provided on a further dedicated adhesive flexible support or is borne in a remote position on a garment worn by the user or in a transport bag, carried by the user.

In combination with one or more of the preceding embodiments and embodiment variations, the interface unit is directly integrated or associated to the control unit or it is part of a separate device and independently communicating with said control unit.

An embodiment variation can also provide that the interface unit is mounted on a flexible support or consists of a mobile device such as a tablet, a phablet or a smartphone or a dedicated medical device.

In all the specified embodiments and embodiment variations, the communication can occur both by cables or wireless.

Each unit, such as the interface unit, the control unit and/or the generator can have its own power source in the form of battery or the source can be shared by all the aforesaid units or by a part thereof.

The power source can be a rechargeable battery or a normal replaceable battery and comprises, in combination, an openable housing and in which the replaceable batteries are mountable and demountable.

A preferred embodiment provides that the power source or sources are connected to respective consumptions, i.e. the above specified units by means of electrical conductors, such as cables or the like.

Still according to an embodiment, a communication by cable is also preferred between the outputs of the single channels of the generator and the corresponding electrodes.

In this case, the conductors or electrical cables are integrated in the structure of the adhesive flexible support, such as for example flexible conductive lines.

Another embodiment variation, which can be provided in combination with any one of the preceding embodiments and embodiment variations, provides that also the control unit can consist of a mobile unit of the user such as a tablet, a phablet, a smartphone, or the like, which executes a control program loaded therein that encodes instructions for the processor and the peripheral units of the mobile unit to take the functions of the control unit.

A further embodiment of the invention provides several stimulation electrodes which are distributed on at least two or more separate flexible supports according to distribution patterns identical between them or different on at least part of said flexible supports.

In this further embodiment, a variant provides a generator for each flexible support and which generator comprises a number of channels corresponding to the number of electrodes present on said flexible support.

Instead, an embodiment variation provides a generator that is shared for all electrodes of all the flexible supports or at least for a subgroup of electrodes of only some or all of the flexible elements. At least one further subgroup composed of all or by part of the remaining electrodes on parts or on all of the flexible supports is connected to the stimulation channels of at least one further generator.

Similarly to that which is provided above for the control units, an embodiment variation which can be provided in combination with any one of the preceding embodiment variations provides a separate control unit for each stimulation pulse generator.

An alternative variant provides a shared control unit for at least part of the generators and at least one further unit for all or at least part of the remaining generators.

Similarly to that which is described above with respect to the first embodiment, each generator or one generator of each group of generators can be directly associated to its own control unit, in this case the control unit being mounted on the same flexible support of the generator or generators.

In alternative, the control unit consists of a remote unit that can be mounted on a flexible support dedicated for one or more control units.

As far as the units interfacing with the control unit are concerned, that which is described above is also described in these variants and embodiments and i.e.

A first variant provides interface units directly associated to a corresponding control unit or interface units that are part of mobile devices separate from the control units.

Also in this case, the control and interface units can consist of a mobile device of the user such as a tablet, a phablet or a smartphone where a control program and/or interface program is/are loaded and executed thereby.

In this case, the communications can also occur by cables or by wireless communication, being preferable to provide connections by cable between the power supplies and the units that are energized by them and between the generators and the corresponding electrodes as described above.

Like in the first embodiment, also in the presence of several generators and/or several groups of stimulation electrodes subdivided on more separate and independent flexible supports, the power sources can be separate for each single generator, for each single control unit and/or for each single interface unit or can be shared between one, two or more of said units.

The power source or sources can be directly coupled with a generator, a control unit and/or an interface unit or can be replaceably or rechargeably mounted on a dedicated adhesive flexible support, the possibility to mount only one power source on a flexible support or more than one power source on a same flexible support being provided, said sources each being connected to a different control and/or interface unit and/or to a different generator.

According to an embodiment, the adhesive flexible support comprises, in combination with one or more electrodes mounted thereon, also one or more pockets or blisters housing and transdermally administering drugs, which pockets or impregnated regions are provided adjacent to the electrode/s or in areas interposed between two or more electrodes on the same flexible support.

An embodiment variation can provide that the electrodes are made in the form of annular elements or polygonal frames which surround a central area where there are provided one or more pockets or one or more blisters housing one or more drugs.

Still according to an embodiment, it is possible to provide a prefabricated flexible support having in combination a distribution of electrodes according to a predetermined design and a distribution of pockets and/or blisters housing one or more drugs, a generator having a number of channels corresponding to the number of electrodes and each one of such channels is firmly connected to a corresponding electrode, while the generator is configured so that to control the activation and deactivation of each channel regardless of each one of the other channels according to activation/deactivation patterns transmitted by the control unit.

These activation and deactivation patterns generate on the flexible support a set of active stimulation electrodes whose distribution is corresponding to a distribution intended for the electrical stimulation of a predetermined anatomic region and/or a predetermined disease, therefore making a flexible support adaptable to different conditions of use.

Advantageously, one or more of said patterns can be stored in a memory of the control unit and can be call back by the user and selected and actuated by means of the user interface.

An advantageous embodiment can provide the possibility to change the aforesaid patterns according to contingent necessities.

A further embodiment can provide to add new patterns by loading them from a remote server by means of a connection or from a removable storage unit, such as a USB key or the like.

An embodiment can also provide, in combination with any one of the preceding embodiments and embodiment variations, that the electrodes are provided on a face of the flexible support, i.e. the one intended to adhere to the skin, while on the opposite face a pocket for housing one or more generators and/or one or more control units and/or one or more power sources is provided.

Said pockets can be sealed in a firm way, i.e. so that they cannot be opened, and can be composed of waterproof or waterproofed walls.

It is possible to provide connection sockets for connection plugs at openable and sealingly closable windows provided on said pockets and coinciding with said connection sockets.

In alternative, the pockets can be openable and sealingly closable, for example to allow the removal of the power source, for its replacement or its recharge.

The connections by cable between the single units housed in the firmly closed pockets can consist of conductors firmly integrated in the flexible support.

The configuration of the pockets according to one or more of the preceding variants can also be provided for flexible supports dedicated to only support the control units and/or power sources and/or interface units according to the variants described above.

Still according to an embodiment, instead of providing an adhesive flexible support which in combination comprises an array of electrodes distributed according to a pattern and possibly individually activatable and deactivatable with a distribution of housing pockets or blisters housing one or more drugs, it is possible to provide to separate the flexible support for the electrodes and the adhesive flexible support provided with the distribution of housing pockets and/or blisters for one or more drugs.

In this case, an embodiment provides that the housing pockets and/or blisters for one or more drugs on an adhesive flexible support are distributed in areas spaced from one another, forming a lattice of areas free from said pockets and/or from said blisters which free areas intersect, connecting to one another, while the flexible support for the stimulation electrodes is made in a shape corresponding to said lattice and has stimulation electrodes at predetermined points of said lattice, which coincide with free areas of the flexible support for the pockets and/or blisters housing one or more drugs, the conductors connecting the single electrodes being associated to the corresponding channel of one or more stimulation pulse generators in the branches of said lattice-shaped flexible support.

According to an advantageous embodiment, in this embodiment, to allow to associate the flexible lattice support for the electrodes to the flexible support for one or more drugs, allowing to provide different flexible supports that are different from one another for the drug or combination of drugs, is advantageous as the housing pocket(s) for one or more generators and/or one or more control units and/or one or more power sources and/or an interface unit are provided in the form of peripheral extensions of the flexible lattice support, the conductors connecting said units to one another and the generators to the electrodes being integrated in the structure of the flexible element and the housing pockets of said units and/or generators being applicable on the face of the flexible support for the drugs opposed to the face intended to come into contact with the skin by tilting said pockets in the form of perimetrical extensions and by providing that the contact face of said pockets with the face of the flexible support for the drug or drugs is adhesive.

Instead, an alternative to the embodiment described above provides that the pockets and/or blisters housing one or more drugs are made lattice-like and of a shape and size coinciding with the lattice formed by the free areas between the electrodes provided on a flexible support. In this case, the pocket(s) for one or more generators and/or control units, interface units and/or power sources are provided on the face of the support element opposed to the one bearing the electrodes.

Still according to an embodiment, the apparatus has communication units between the generators, the control unit(s), the interface unit(s) and the power sources which consist of communication units according to a network protocol, preferably self-configuring.

This characteristic is particularly advantageous when a shared control unit is provided for a plurality of generators, each of which or part thereof is associated to a set of electrodes on a flexible support of a plurality of flexible elements.

In fact, in this case, by removing or adding a flexible support with a set of electrodes and with one or more generators dedicated thereto, the network automatically recognizes the presence or absence of the flexible support and can configure itself automatically, simultaneously configuring the generators to emit stimulation pulses synchronized with the ones of the other flexible supports and correspondingly to the type of treatment set.

This function is advantageous both for the possible integrations or modifications of the apparatus in the course of treatment and in the initial setting step, i.e. after the first application of the flexible supports in the regions indicated for the treatment and at the first activation of the apparatus.

The invention has further characteristics and improvements which are object of the dependent claims.

BRIEF DESCRIPTION OF THE DRAWINGS

These and further characteristics and advantages of the present invention will become clearer in the following description of some exemplary embodiments shown in the accompanying drawings, in which.

DETAILED DESCRIPTION OF EMBODIMENTS OF THE INVENTION

In the present description, support element means a foil or a flattened element to which or in which more layers are applied or incorporated by lamination or by embedding constructive parts such as the electrodes, conductors for transmitting signals or pockets for drugs or for electronic circuits.

Moreover, the flexible support elements described are provided with a continuous adhesive layer or in areas for removably fastening to the skin of the human body.

Figure 1:
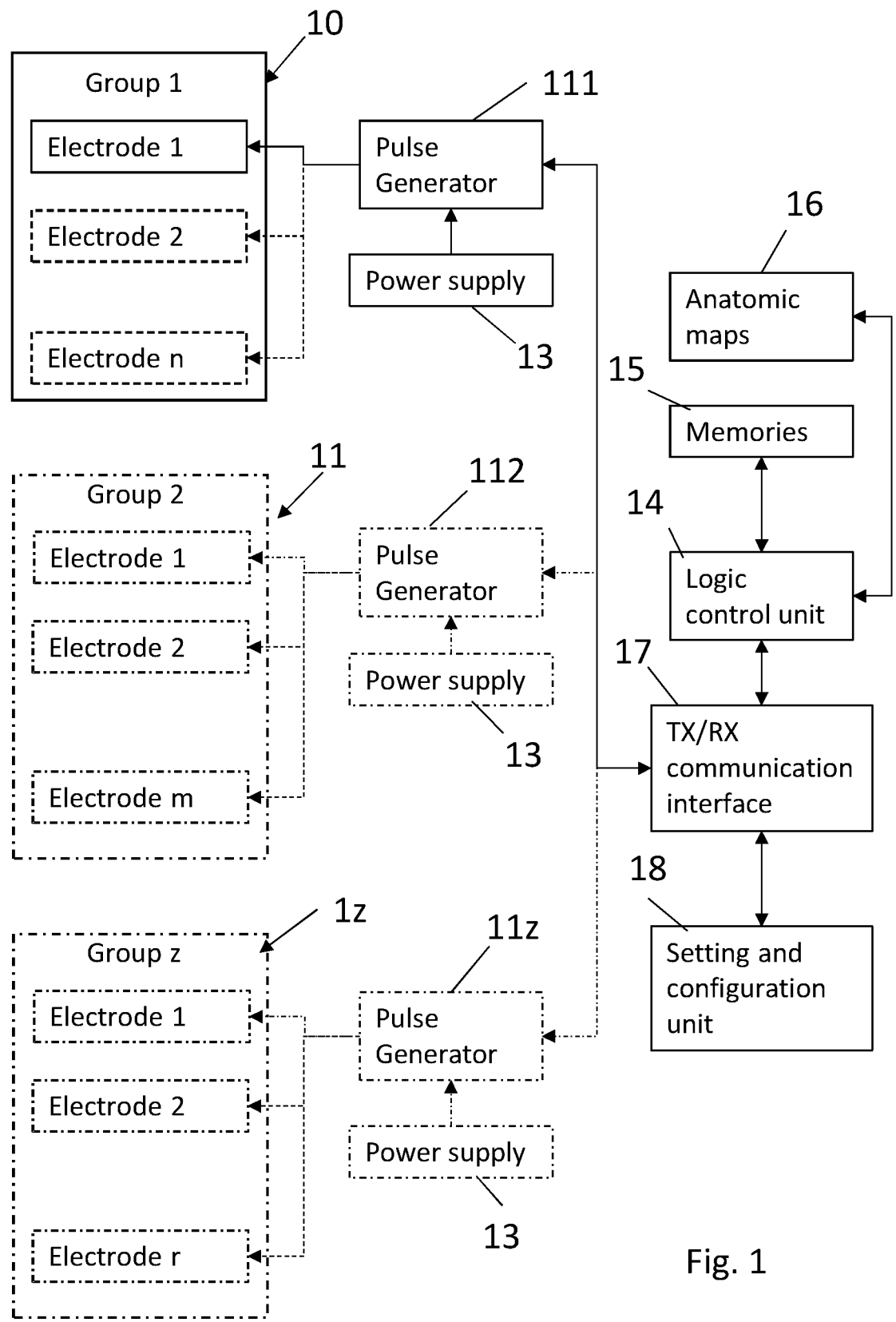
FIG. 1 shows a block scheme of an embodiment of the apparatus according to the invention.

FIG. 1 shows the block scheme of an electrical stimulation apparatus, which according to the present invention is made in the form of wearable apparatus.

The apparatus comprises one or more flexible supports denoted by 10, 11 and 1z. Each of the flexible supports bears one or more stimulation electrodes 1, 2, n or m, or r, the variables n, m, r being indicative of a natural number whatsoever, the single supports 10, 11, 1z being provided with an identical or different number of electrodes. In the embodiment of FIG. 1, each group of electrodes is associated to a generator 111, 112 and 11z with a relative supplier 13. Each generator 111, 112, 11z has a plurality of output channels for a sequence of electrical stimulation pulses and each channel is connected to a corresponding electrode 1, 2, n, m, r. The pulse generator operates under the control of a logic control unit 14.

This logic control unit is configured to provide instructions on the pulses to be generated to the generators in relation to the configuration parameters of said pulses, such as amplitudes, intensities, power, frequency, duration, polarity and combinations of a temporal succession of different pulses for one or more of the aforesaid parameters, as well as to synchronize the pulses of the sequences provided to the electrodes 1, 2, n, m, r of the single groups on the relative flexible supports between them, for delivering through the skin to the patient.

In the embodiment of FIG. 1, a single logic control unit is provided to control in a synchronized way the generators 111, 112, 11r, but as will be clear herein under, in this case it is a possible embodiment variation, being it possible to provide alternative architectures which provide two or more control units dedicated to a single generator or subgroups of generators and which operate in a synchronized way between them by automatically negotiating the temporal control sequences of the generators between them.

The logic control unit 14 can be made both in the form of dedicated hardware in which the control logic of the generators is firmly integrated according to one or more options which can be selected, but which are substantially fixed.

Instead, a preferred variant provides that the logic control unit consists of generic hardware comprising a processor and peripheral unit and that the logic control unit 14 executes control software which is stored in a memory 15. With regard to the specific application of the stimulation apparatus, the memory 15 can contain databases of different settings corresponding to different types of treatments, both for that concerning the anatomic region and for that concerning the effects for which the treatment is targeted.

Advantageously, a storage area 16 is dedicated to anatomic maps for the positioning of the electrode or electrodes and/or of the support(s) 11, 12, 1z in relation to the different types of treatments desired.

A communication interface 17 allows the control unit to transmit control signals to the single generators 111, 112, 11z and to a setting and configuration unit 18, i.e. to a man-machine interface unit which allows to execute maintenance, setting and manual configuration operations as well as to carry out upgrade activities of the program executed by the logic control unit 14 and/or of the databases of the treatment protocols and/or of the anatomic maps for positioning the electrodes and possibly also to execute diagnostic activities of the units of the apparatus. The communication can take place both by cables and by radio, i.e. wireless.

The selection of the communication mode and protocols among those currently known to the technician of the art is a pure selection of opportunities driven by the necessary band width, necessary signal power, energy resources provided by the power source and depends on the type of architecture of the apparatus and on the type of treatment that needs to be carried out.

The setting and configuration unit 18, i.e. the interface unit, can consist of a remote unit, such as for example a mobile device available to the user. This can also be a mobile device of the currently known type in which an application is installed that, once executed, configures the mobile device to execute the functions of the interface unit 18 of the apparatus.

Particularly advantageous examples of this type of mobile units can be devices such as smartphones, phablets, tablets or similar devices.

An embodiment variation not shown can also provide that the control unit 14 does not consist of a unit having dedicated and separate hardware, but of hardware composed of that of a mobile device such as for example one of the aforesaid ones and which also executes an application containing instructions for configuring said mobile device to execute the functions of the logic control unit.

It is clear how, in this case, the user interface and the logic control unit, i.e. the units 14 and 18 as well as the memories 15 and 16 and the communication unit 17 are integrated in a single device which the user often already possesses and which normally has hardware resources able to satisfy the processing power required by the control, communication and interface software and the memory necessary for the data described above.

Figure 2:
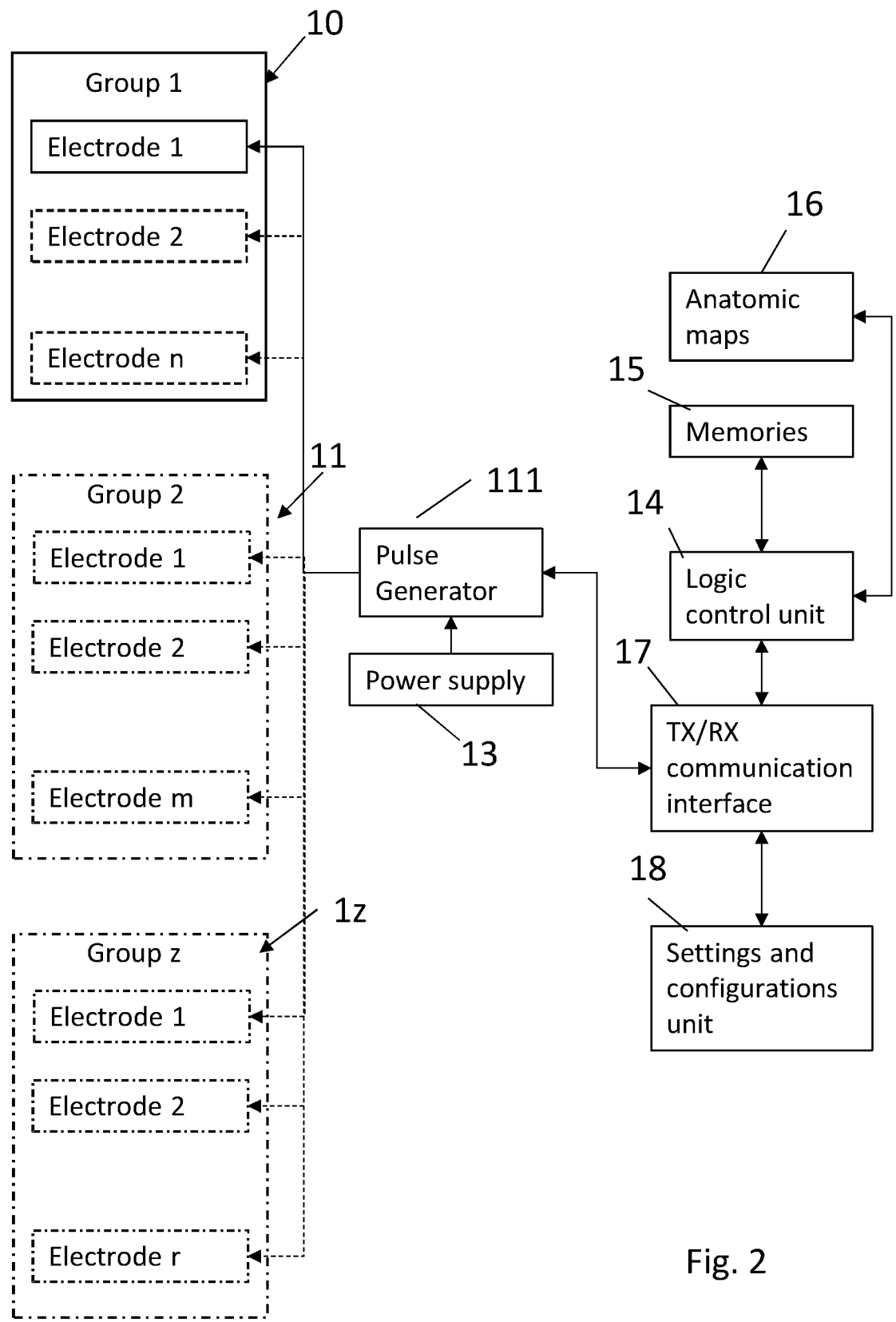
FIG. 2 shows an embodiment variation of the embodiment according to FIG. 1.

FIG. 2 shows an embodiment variation which provides a different architecture. In this case, the electrodes on the flexible supports 11, 12, 1z are each connected to a dedicated channel of a shared generator 111.

The generator can be mounted on a flexible support intended to bear the electrodes, for example the support 11 can be mounted on a dedicated adhesive flexible support for example of the type shown in FIG. 8 and which will be described hereunder.

The adhesive flexible support and the electrodes 1 can be made in different ways.

An embodiment can provide a supporting thread, for example of cloth or plastic material, on one of whose faces a layer of adhesive material is applied. An electrode can be composed of a leaf of conductive material cut to a predetermined shape and size and applied to the adhesive material. Each pole of each electrode is made from a leaf-shaped piece of electrically conductive material and a power conductor, for example in the form of a band of conductive material, is connected to each pole.

The leaf-shaped pieces of conductive material can be fixed to the adhesive layer, also the conductors or conductive bands. The latter are further covered to be electrically insulated towards the outside by a band of plastic material, for example a double-sided adhesive band, which overlaps the conductors or conductive bands by adhering against them and against the adhesive layer of the flexible support on one side, while the other face of the double-sided adhesive band restores the continuity of the adhesive layer at the path of the conductors.

Different further constructive embodiments are possible, for example it is possible to provide that the single layers are laminated one on the other or that the conductor elements are fixed in a female die of plastic material by molding. A further variant can provide for the making of the poles of the electrodes and/or the conductive lines by applying the same with electrically conductive liquids that are sprayed to form the poles and conductive lines thereof.

Figure 3A:
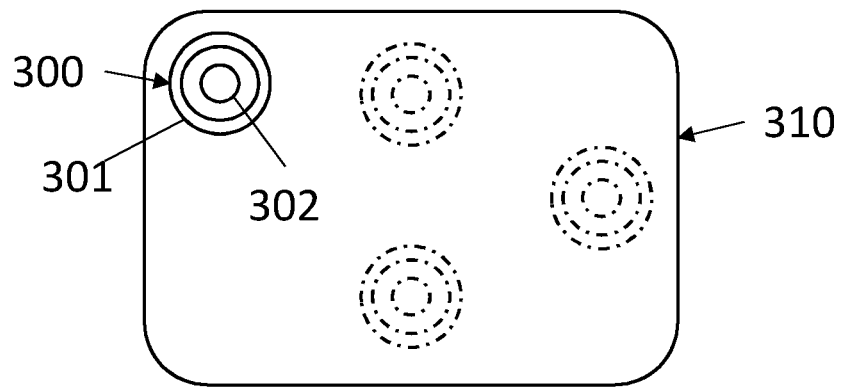
FIGS. 3A, 3B, 3C show three embodiment variations of a flexible support with a distribution of electrodes that can be provided in the electrical stimulation apparatus according to the present invention.
Figure 3B:
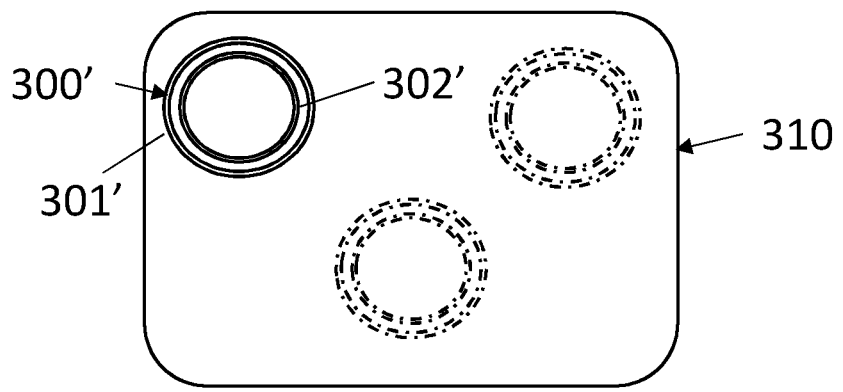
Figure 3C:
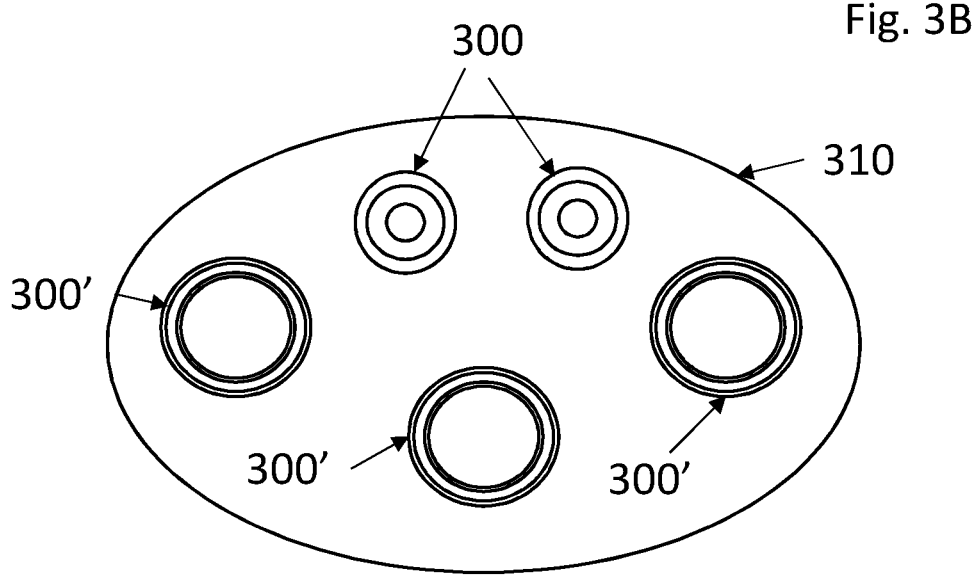

FIGS. 3A and 3C show three different embodiment variations.

A flexible support of the band aid type is shown in FIG. 3A with a plan view of the face intended to come into contact with the skin. The electrode 300 comprises two poles 301 and 302 of which one central and one annular surrounding the central one. The adhesive layer can be provided only around the annular pole 302 and not between the latter and the central pole 301, or it is possible that the adhesive layer is also present in the intermediate area between the two poles 301, 302.

The flexible and adhesive support element can have a plurality of electrodes thereon, as is depicted with the further electrodes shown with dashed and dotted lines.

Both the number of electrodes 300 and the distribution pattern of the same on an area defined by the plan shape of the flexible support element 310 can vary depending on the needs to set a specific treatment.

As will become clearer hereinafter with reference to FIG. 7, the electrical stimulation apparatus can comprise a plurality of said flexible supports 310, which can be identical between them or partly different between them and which are applied in different regions of the body correspondingly to the instructions for the specific application.

In the variant of FIG. 3B, the electrode 300' is formed by two poles 301' and 302' which are annular and concentric and leave a free area inside them.

The variant of FIG. 3C instead shows a flexible support element 310 of oval or elliptical shape and which comprises a plurality of electrodes made according to the two different types of the examples according to FIGS. 3A and 3B.

The examples shown are not exhaustive and instead show the high versatility of the shape and distribution of the electrodes. This must be modified at least on each flexible support element depending on the specific treatment to be effected and depending on a protocol provided for the specific treatment.

A further embodiment provides that the flexible support element, or at least a part of these elements, is provided not only with the electrodes, but also with pockets or blisters for containing one or more drugs which are administered transdermally thanks to the diffusion when the walls of said pockets or blisters come into contact with the skin.

Also in this case, different distribution configurations are possible both for the electrodes and the pockets and/or blisters containing the drug or drugs. These depend on the type of disease to be treated and on the treatment provided.

Figure 4:
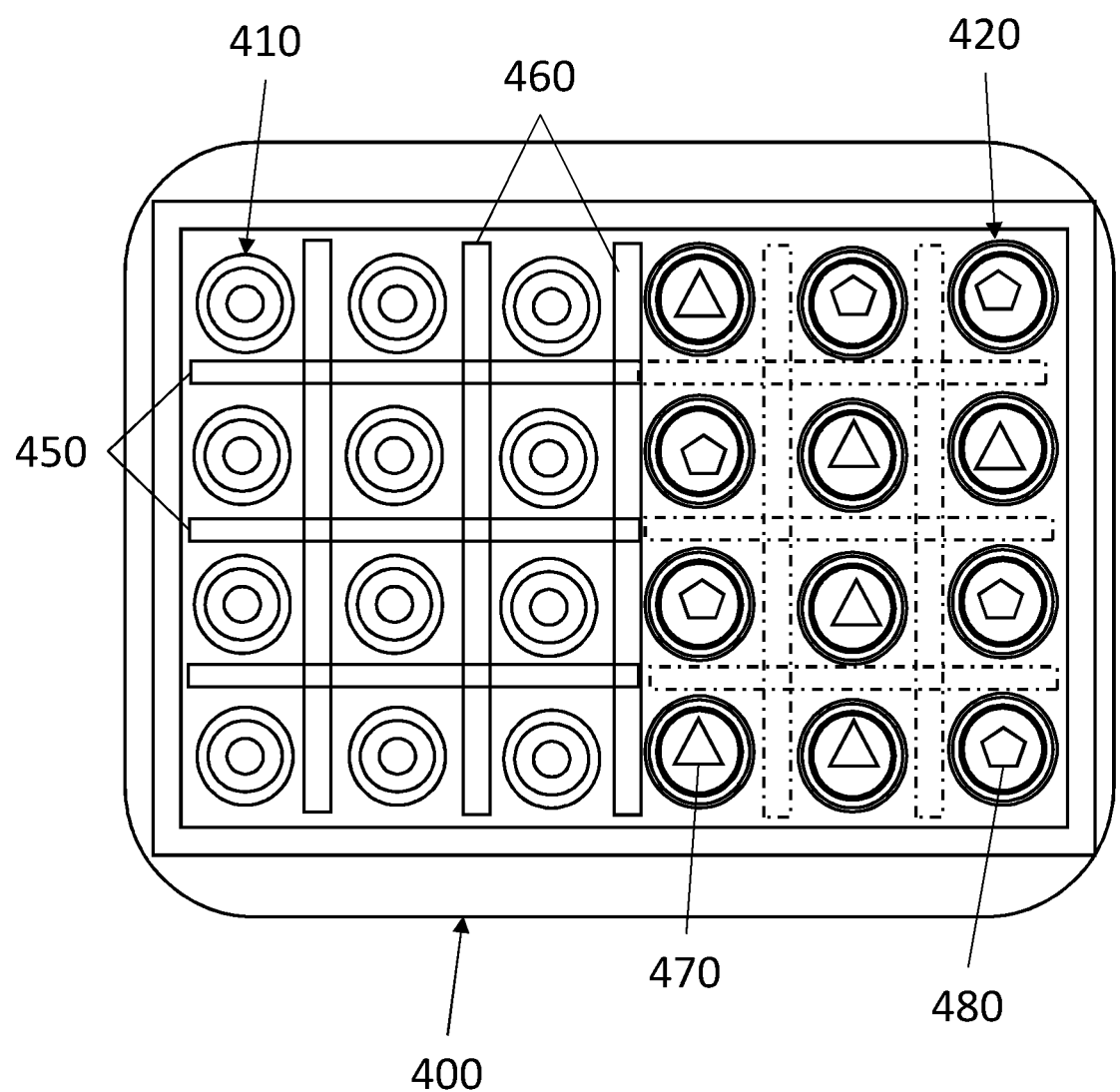
FIG. 4 shows a view of the contact side with the skin of a further embodiment of a flexible support according to the present invention which provides, in combination, housing pockets and/or blisters for one or more treatment drugs associated to the electrical stimulation treatment and in which the left half and the right half are different for their different types of electrodes.

FIG. 4 shows by way of example two alternative configurations which are respectively shown in the left half and in the right half of the flexible support element 400.

In the left half, the flexible support element 400 has a set of electrodes arranged according to a matrix arrangement on rows and columns. The electrodes 410 are arranged spaced from one another and are of the type shown in FIG. 3A. In the right half, however, the electrodes 420 are of the type shown in the example of FIG. 3B. These electrodes are also arranged according to a matrix order on rows and columns.

It is important to underline that this arrangement is only a specific example of the different possible variants and that it does not constitute a limitation of the inventive concept.

In the left half of FIG. 4, said pockets or said blisters 450, 460 are provided between the rows and columns of electrodes 410, while in the right half, the pockets or blisters 470 and 480 are provided inside the two concentric poles of the electrodes 420.

Moreover, in the right half, in order to show the possibility to provide a combination of different drugs in different areas of the element 400, the pockets or blisters 470 and 480 are also graphically different from one another.

The two solutions can also be provided in combination. This way for example, the pockets or blisters similar to those 450 and 460 are shown in the right half with dashed and dotted lines to symbolize the possibility that one or more of these is present.

With reference to the example of FIG. 3C, combinations of electrodes 410 and 420 and of the relative pockets or blisters 450, 460, 470 and 480 can also be provided on the support element 400.

Figure 5:
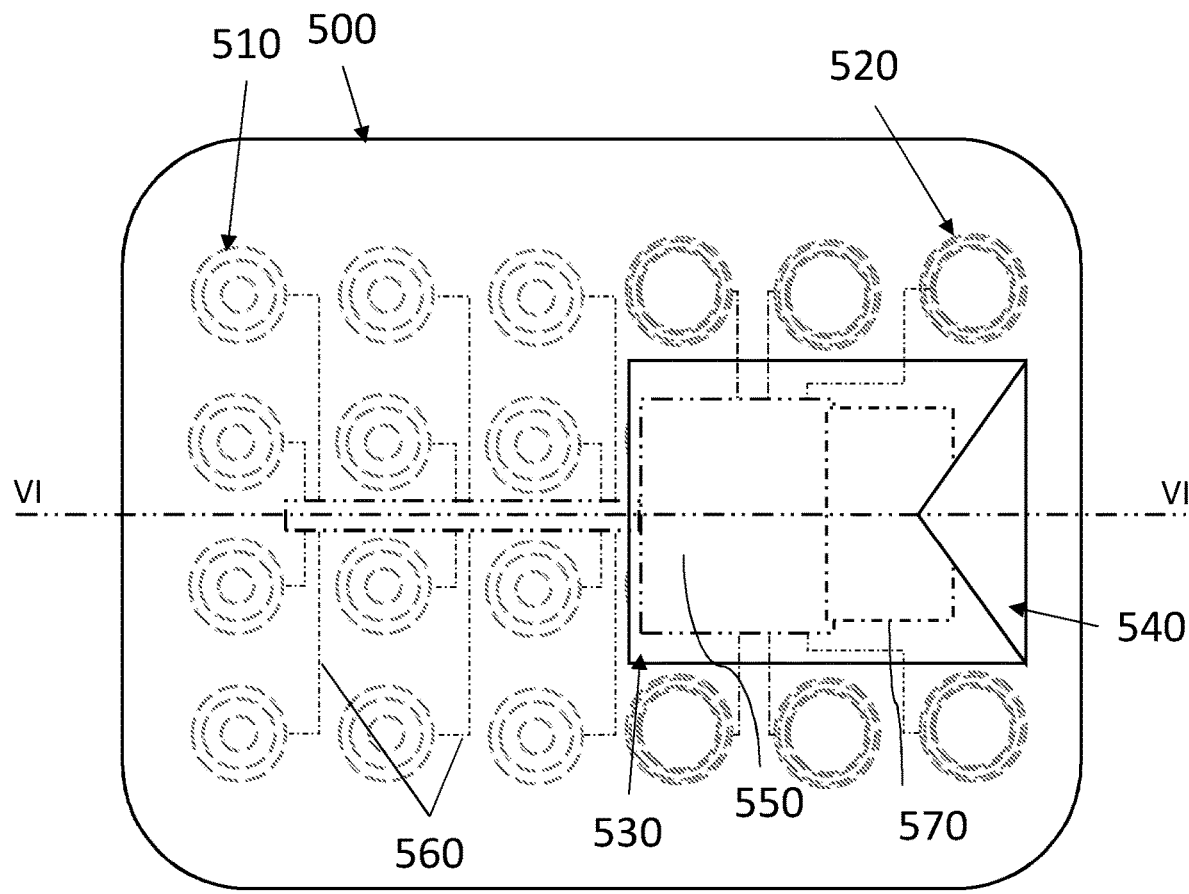
FIG. 5 shows a plan view from above of a flexible support embodiment which is provided with a openable pocket for housing the generators and/or further control units and/or power sources.

FIG. 5 shows an exemplary embodiment of a flexible support element similar to the one of FIG. 4. In this case, the face opposite the one adhering to the skin is shown. The flexible support element 500 has a plurality of electrodes also here according to two alternative embodiment examples like in FIG. 4 and which are denoted by 510 and 520. A pocket 530 is present on said side of the element 500. The pocket is openable and closable by means of a closing flap 540 which is superimposable to the opening and a strap which surrounds said opening on the stationary of the pocket 530, as also results in FIG. 6.

Inside the pocket, a generator 550 is shown in transparency. The generator 550 has a channel for each electrode. Each channel connects separately with a dedicated line 560 to a corresponding electrode.

The pocket 530 is openable since a power source 570 which is demountable from the generator 550 is associated thereto, mechanical coupling and simultaneous electrical connecting means of the electric source 570 to a socket of the generator being provided.

The opening of the pocket is provided in order to allow the replacement of the spent power source 570 with a charged one and/or to recharge the power source by means of a cabled connection to a recharging unit (not depicted).

The flap 540 can be provided with sealingly removable adhesion means at the stationary part of the pocket 530, so that to make the pocket 530 sealed against humidity and/or resistant to water infiltrations, for example when the user wearing the apparatus is washing himself.

The unit 550 can comprise both the generator and for example the control unit itself and a unit communicating with the user by a mobile interface unit, according to one of the embodiment variations described above.

In this case, the element 500 according to FIG. 5 constitutes the entire electrical stimulation apparatus and is able to operate autonomously, obviously being activatable and deactivatable by means of the mobile terminal of the user (not depicted).

In this configuration, in case two or more elements 500 must be provided, each configured according to the preceding example in which they work autonomously, it is possible to allow for example that the control unit also operates as the self-configuring communication network unit and that said communication unit allows the single control units to recognize the presence, identify the anatomic part on which they operate, negotiate and elect among the same a master control unit which coordinates and synchronizes the further control units to generate sequences of pulses synchronized between them, as required by the various treatment protocols, in order to allow a synchronization of the stimuli generated by the various elements 500.

Figure 7:
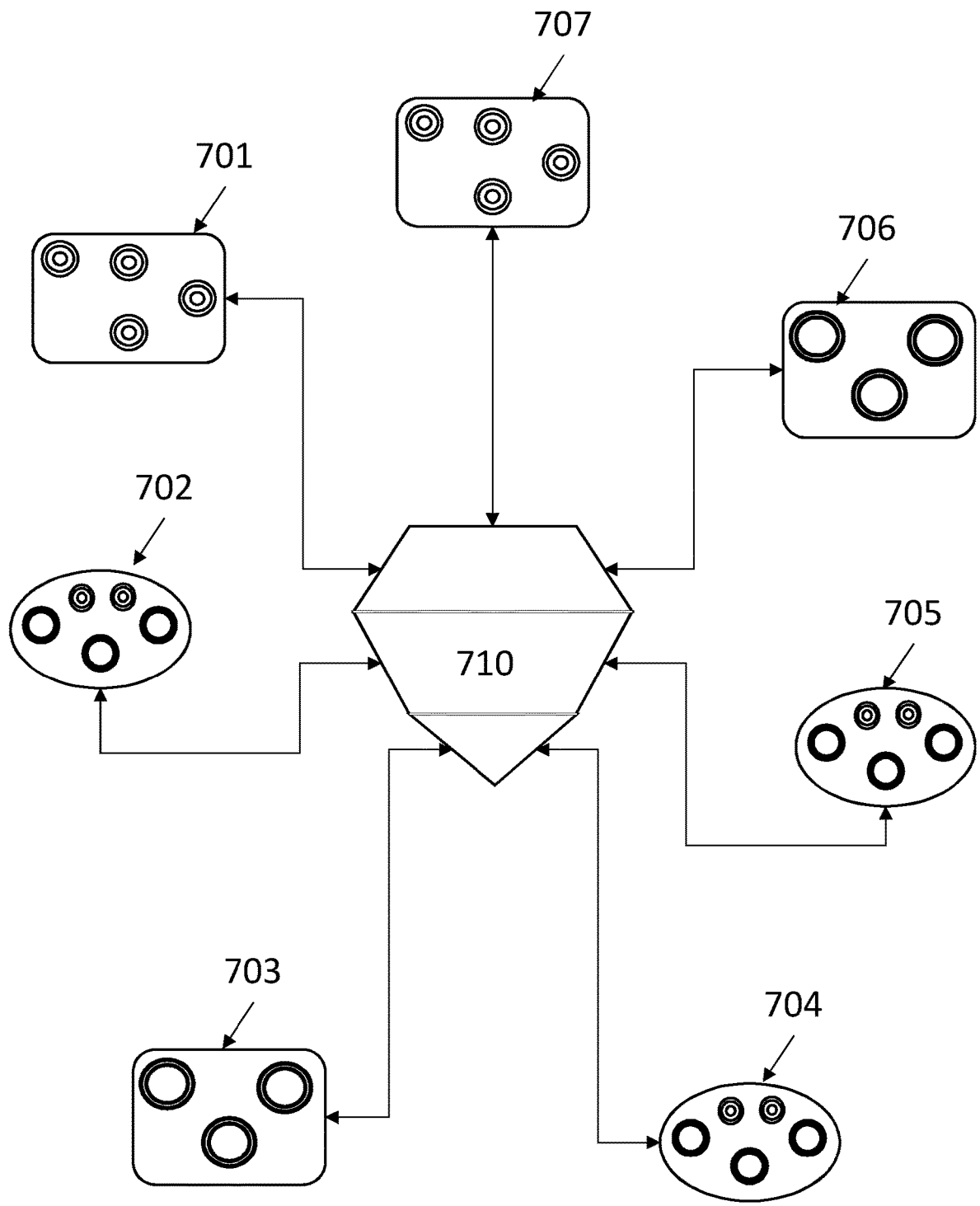
FIG. 7 shows a main block scheme of an embodiment of an electrical stimulation apparatus according to the present invention.

In the example of FIG. 7, the apparatus comprises six separate flexible elements 701, 702, 703, 704, 705, 706, 707 each of which bears at least one own generator (not visible) and a specific distribution of electrodes and/or pockets or blisters for one or more drugs.

Each stimulation pulse generator is connected to a central control unit 710 similarly to the architecture according to the block scheme of FIG. 2.

An embodiment variation can provide that the control unit 710 is integrated with an interface unit in a mobile device of the user, such as a smartphone, a phablet or a tablet or to a specific mobile device. In this case, the generators are provided with communication modules of the wireless type with which they receive the execution commands and transmit the status signals to the mobile unit. In case of a smartphone use, the functionalities of the control unit and of the user interface are obtained thanks to the execution of a specific application that must be installed on the mobile unit.

It should be noted that the connections between the control unit 710 and the single elements 701 to 707 do not denote physical cabled connections, or better, do not exclusively denote this type of connections but represent a generic connection which can also be a wireless connection of any type and with any protocol known today.

An embodiment variation can provide that the control unit 710 is in the form of specific hardware and intended to be supported by the user.

Figure 8:
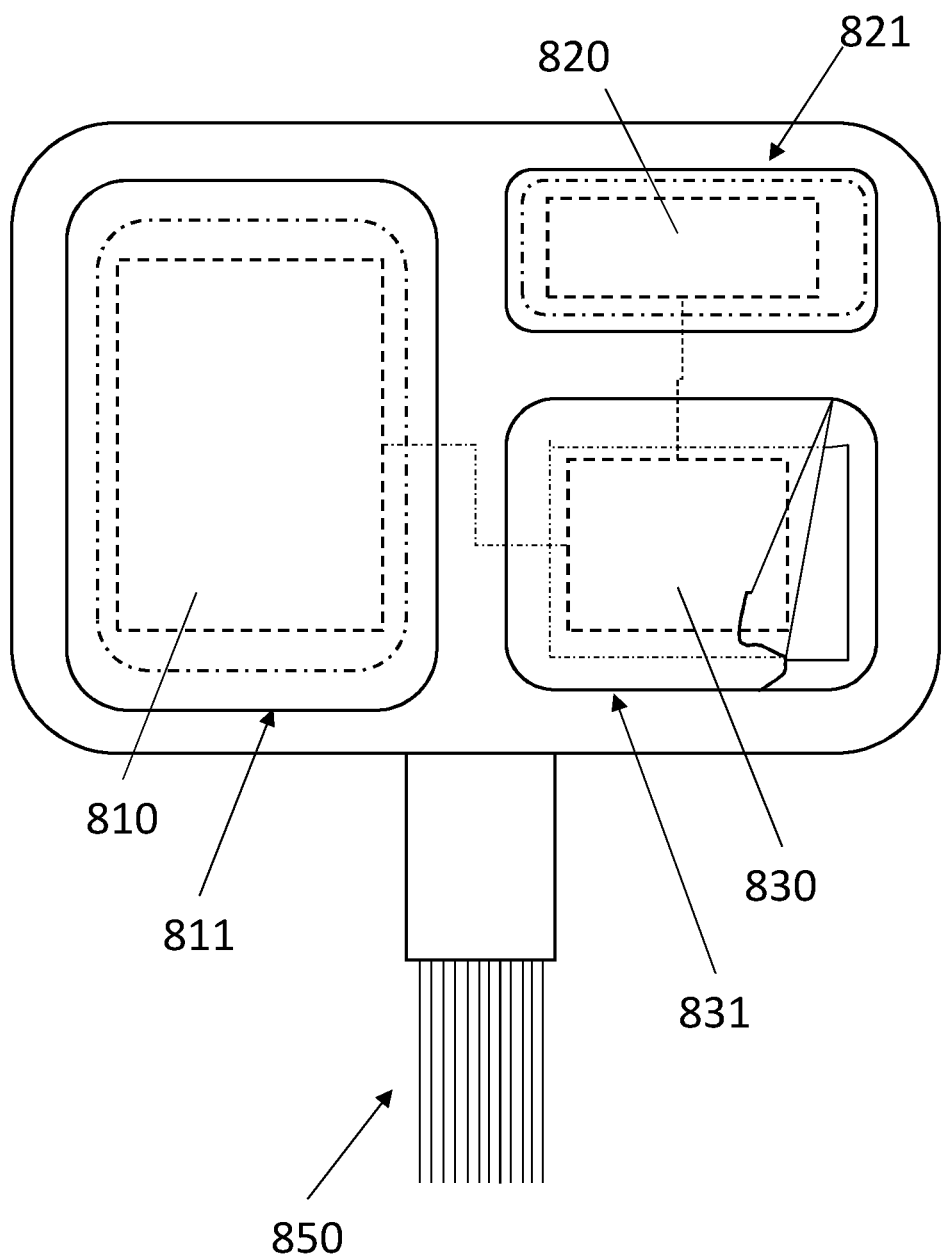
FIG. 8 shows an embodiment of an adhesive flexible support for a control unit, the communication unit with an interface unit and with a power source provided in the example of FIG. 7.

A possible embodiment of this last variant is depicted in FIG. 8. The respective circuits of the control unit denoted by 810, of the transmitting and receiving communication unit 820 and of the power battery 830 are each housed in a corresponding pocket 811, 821 and 831.

As depicted, at least the pocket 831 of the power battery 830 is made openable to allow its replacement with a charged battery.

Alternatively, one or more of the further pockets can be openable or also the pocket of the battery is not openable, but the battery is of the rechargeable type and has access from the outside to a connection socket with a recharging power supply.

In an embodiment, this socket on the battery can be accessible through a window (not depicted) in the walls of the pocket 831 which can be openable or closable or always open.

The pockets 811, 821 and 831 are provided for example on a flexible support element 800, for example of the adhesive type such as those bearing the electrodes.

FIG. 8 shows a variant in which the connection of the control unit 810 with the generators is made by means of independent electrical conductors for each generator and that are denoted by 850.

Said conductors extend until connection connectors of the generators present on each support element for the electrodes and bear corresponding connection plugs.

Figure 6:
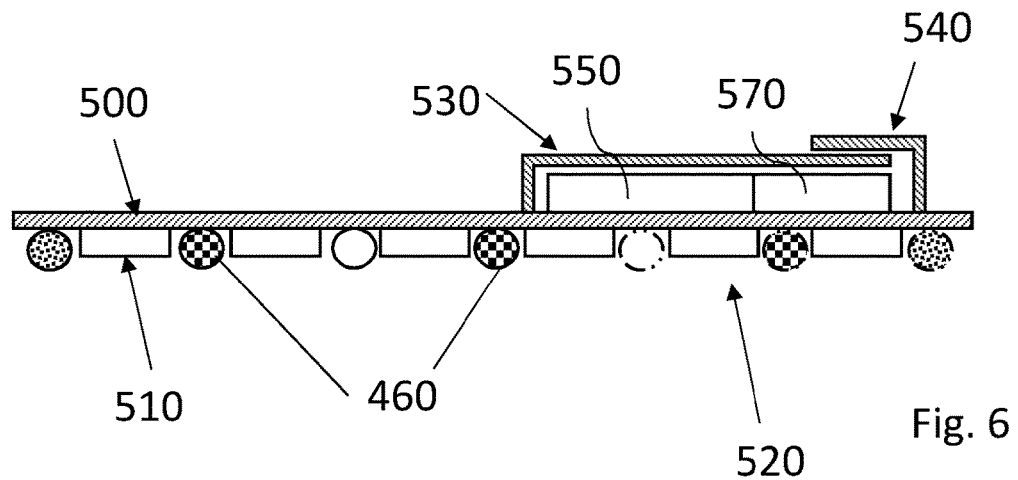
FIG. 6 shows a section according to a plane perpendicular to the sheet and along the line VI-VI of FIG. 5.

With reference to the embodiment of FIGS. 4 to 6, it is clear that by having an orderly set of electrodes available, which are arranged on rows and columns, it is possible to generate different distributions of electrodes alternative from one another on the surface of the flexible support element. This can simply takes place by enabling or disabling one or more electrodes of the set. This way only the enabled electrodes shall receive the electrical stimulation pulses to be transmitted to the body.

The enabling and/or disabling of each single electrode can occur at different levels. An embodiment provides the enabling or disabling of the channels by the generator itself and on command of the control unit or the user directly from the interface unit.

Still according to a possible variant, so that to ensure that the electrodes and corresponding power supply conductors and the pockets or blisters for one or more drugs are firmly provided on the same flexible support element, it is possible to provide two different support elements complementary and couplable and decouplable between them.

In an embodiment similar to the one of FIGS. 4 to 6, the pockets or blisters 450 and 460 for one or more drugs are mounted on a separate support element in the form of a grid, which grid has dimensions corresponding to the interspaces between the electrodes 410. In turn, these are provided on a separate support element similar to the one 400 to which a grid-like support element comprising the pockets or blisters for the drugs is applied before being applied to the patient.

Figure 9:
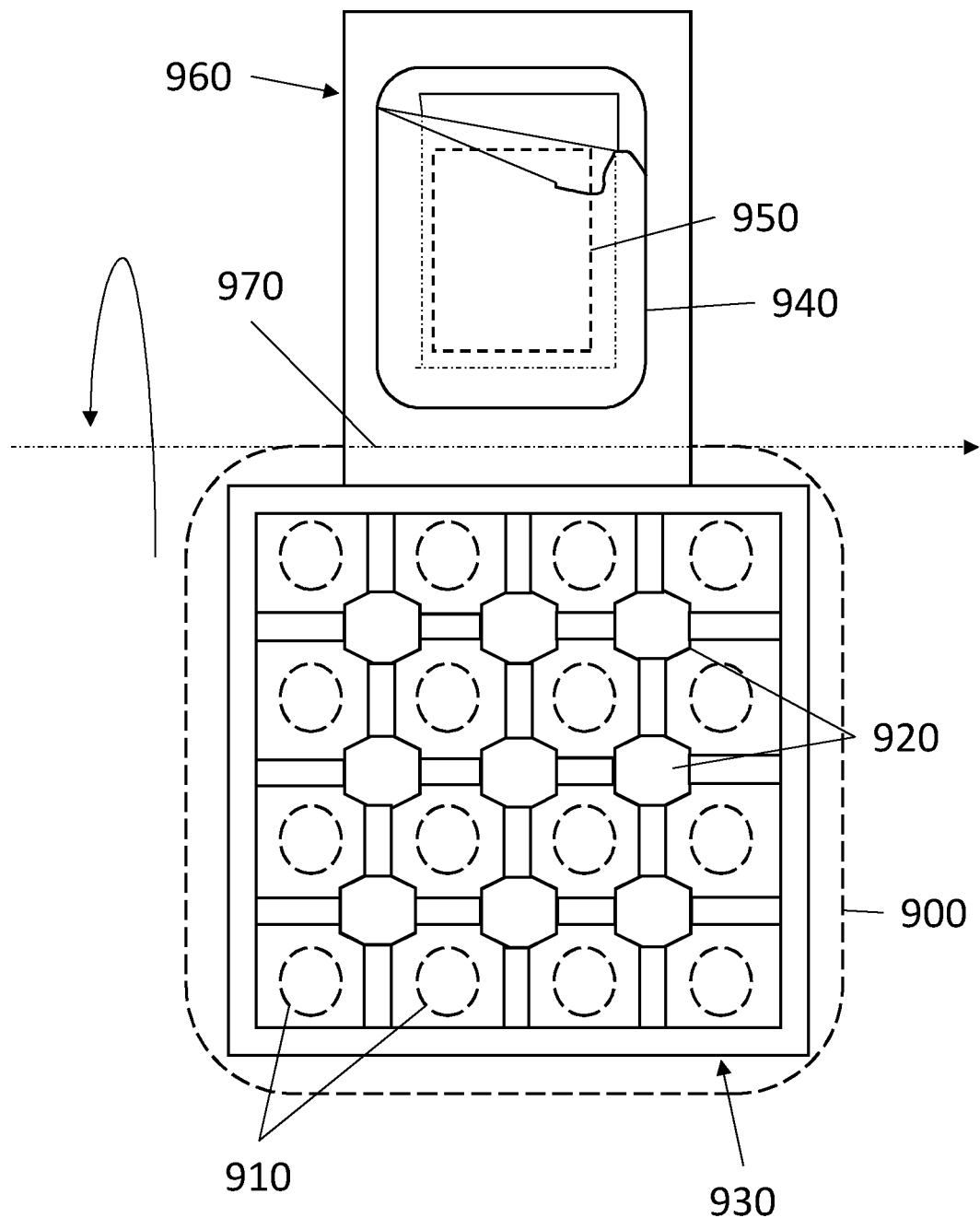
FIG. 9 schematically shows a plan view of the face adhering to the skin of a flexible support for stimulation electrodes and with pockets or blisters for housing one or more drugs, in which the flexible support for drugs is separated from the flexible support for the stimulation electrodes and which two supports are couplable in a separable way to one another.

In the variant of FIG. 9, the situation is inverted. The pockets or blisters for one or more drugs denoted by 910 are provided on an adhesive flexible element and are distributed on rows and columns in a position spaced from one another, while the electrodes 920 are provided on a flexible element 930 in the shape of a grid and which is intended to overlap the free areas between the single pockets and blisters 910 for the drugs on the element 900.

In FIG. 9, the two layers formed by the element 900 with the pockets 910 for the drugs and the element 930 with the electrodes 920 are shown, the first being depicted with discontinuous lines, whereas the element 930 and the electrodes 920 are depicted with continuous lines.

In this case, since it is not possible to provide any pocket housing the electronic circuits such as the generator, control unit, communication unit and power supply on the face of the grid-like flexible support element 930, since it would remain interposed between the element 900 and the one 930, the pocket 940 for one or more of the aforesaid units, for example for a generator 950 and the possible power source (not shown in detail) is made in a peripheral flap 960 departing from a side edge of the grid-like support element 930 supporting the electrodes 920 and which has a folding line 970 substantially coinciding with or side by side to a corresponding peripheral edge of the support element 900 for the pockets and blisters for a drug. Therefore, by coupling the two support elements 900 and 930 to one another as shown in FIG. 9, the flap 960 can be folded on the face of the support element 900 opposed to the one coupling with the electrodes.

The flap 960 can be provided with an adhesive coating on the face in contact with the upper face of the support element 900.

Thanks to these two embodiment variations it is possible to provide to combine the electrical stimulation apparatus with different combinations of drugs depending on the treatment provided, without having to provide each flexible support for the drugs of an integrated distribution of electrodes of the conductors connecting to the channels emitting the stimulation pulses of one or more generators and of said one or more generators.

Moreover, by providing a suitable formulation of the coupling adhesives, it is possible to make the support element for the electrodes separable from the one for the drugs and therefore reusable in combination with other drugs or with a new drug dosage, when the previous one is empty.

Still according to an embodiment, the apparatus provides a flexible support of an essentially annular shape that can have any shape such as the circular, elliptical, oval or also polygonal one.

On the annular shape, it is possible to distribute one or more electrodes 102, one or more further sensors 103 selected from one or more sensors of the following list: pH sensors, temperature sensors, $pO_2$ sensors, dermal impedance sensors and/or combinations thereof.

Like the electrodes, the sensors are also in contact with the skin.

In addition to the sensors and electrodes, the annular element will bear at least for part of their length the conductors connecting them to the control units.

Figure 10:
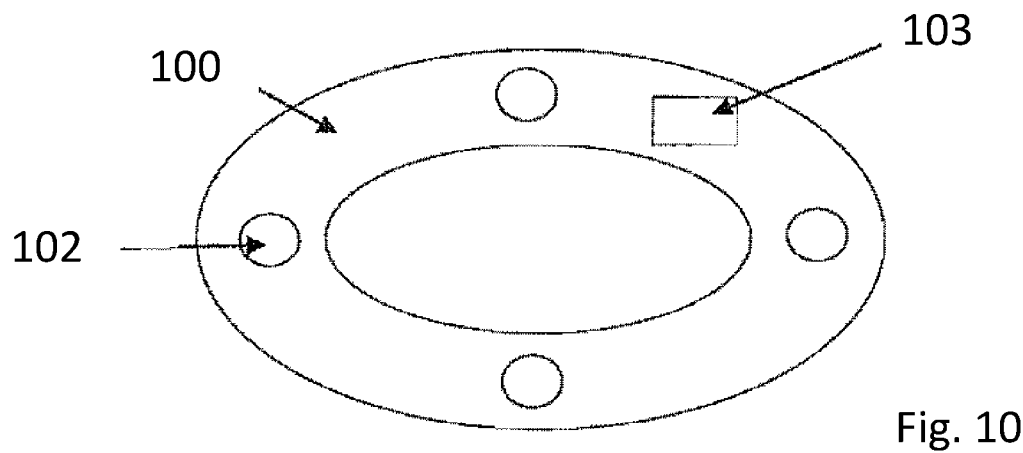
FIGS. 10, 11 and 12 schematically show the three layers of an embodiment of a flexible support for a device according to the present invention.
Figure 11:
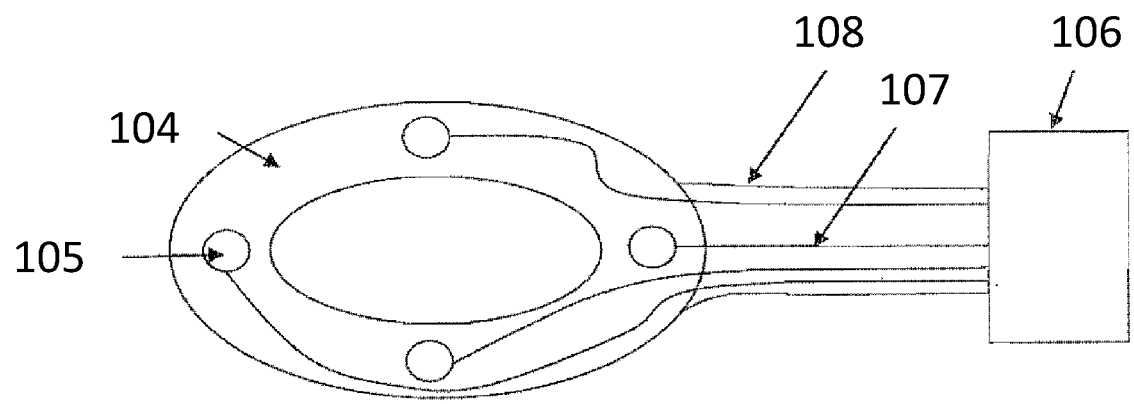
Figure 12:
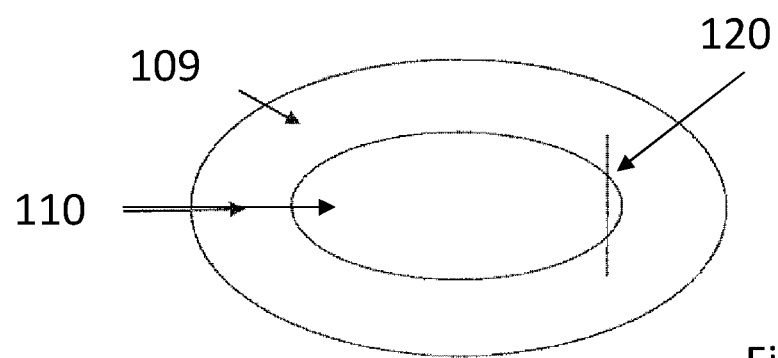

Still according to a further advantageous characteristic, the flexible support can be made multilayer as shown in FIGS. 10 to 12. In this case, a first layer consists of the skin contact layer 100. This layer is made of biocompatible material, such as preferably polyurethane material.

Said material can advantageously be further pervious to gases and is provided with an adhesive layer on the part intended to come into contact with the skin.

According to an embodiment, the adhesive is of medium grade.

Still according to a further embodiment, said layer is of transparent material and/or of thin thickness and anyhow so that to result sufficiently plastic to allow its deformation both in the skin application and in movement.

The annular element 100 has specific housing areas of adhesion to one or more electrodes distributed angularly along the angular extent of said ring 100.

These housing areas consist of Ag—Cl gels and generate the contact between the electrode borne by the ring 104 and the skin of the patient. In addition to the electrodes, the ring also has housings for the fastening of one or more of the sensors previously described and listed.

The second layer 104 of the flexible support is shown in FIG. 11. The second layer has an annular shape, i.e. toroidal, essentially congruent to the one of the first layer and adheres by chemical and physical adhesion to said first layer. The second layer is a non disposable system of more rigid material, preferably of biocompatible polyurethane.

According to a preferred embodiment, also the second layer is of a material pervious to gases and includes the circuitry part denoted by 107, 108.

Preferably, said circuitry part is made of the flat cable type.

The ring 104 of the second layer bears a corresponding electrode 105, which adheres in contact with the gel of said areas 102, in a position coinciding with the areas 102 of the first layer.

A remote control unit 106 drives the electrodes. The unit 106 works as a receiver and transmitter and has a skin contact surface which is also made of biocompatible material, preferably biocompatible polyurethane.

According to a preferred embodiment, said material is also adhesive on the skin contact surface.

In combination with the adhesive layer, it is possible to provide a mechanical fastening by tightening thanks to an elastic non-adhesive strap, such as a strap provided with a closure of the Velcro type, automatic buttons or the like. This strap denoted by 140 in FIGS. 13 to 15 works as a securing fastener of the unit 106.

The cables 107, 108 can be connected to the electrodes by bayonet connections.

The embodiment shown in the figures has a third layer denoted by 109 in FIG. 12, in addition to the first and second layer.

According to an embodiment, this third layer is of disposable material and works to cover the second layer shown in FIG. 11 towards the outside.

According to a further characteristic, the third layer can further also cover the central area of the annular shape of the two underlying layers by also extending along said central part.

Advantageously, the central part is kept raised with respect to the skin by the thickness of the two underlying layers.

Still according to an embodiment, the third layer 109 can be a closing and opening element of said central area of the annual shape of the underlying layers. Said central area denoted by 110 being intended to receive the lesion to be treated.

In an embodiment, on a side of said central area, the third layer is provided or is shaped so that to form a zipper as schematically depicted by the line 120. Said zipper is advantageously elastic and works to allow repeated closing and opening actions, for example to allow the replacement of medications or the like.

According to a preferred embodiment, the material of the third layer has more rigidity than the first layer and is anyhow of biocompatible and/or pervious to gas material.

Still according to an embodiment variation, it is possible to provide that, inside the window delimited by the annular layers, a removable biocompatible polyurethane sponge layer can be provided, which has a predetermined thickness and a predetermined ability to absorb liquids, in particular for the removal of the exudate by periodic replacement.

Figure 13:
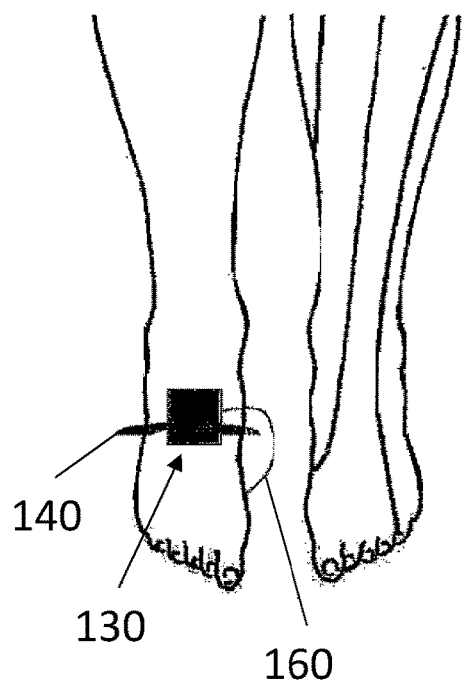
FIGS. 13 and 14 show an application of the apparatus made according to the embodiment of FIGS. 10 to 12, in which the apparatus, i.e. the adhesive flexible support, is applied to the sole of the foot.
Figure 14:
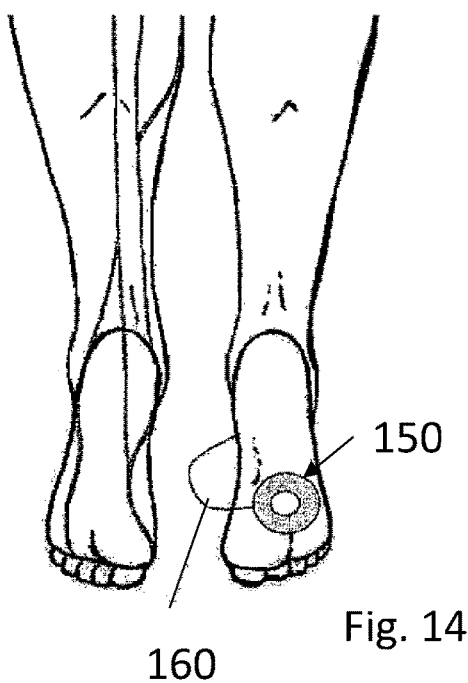
Figure 15:
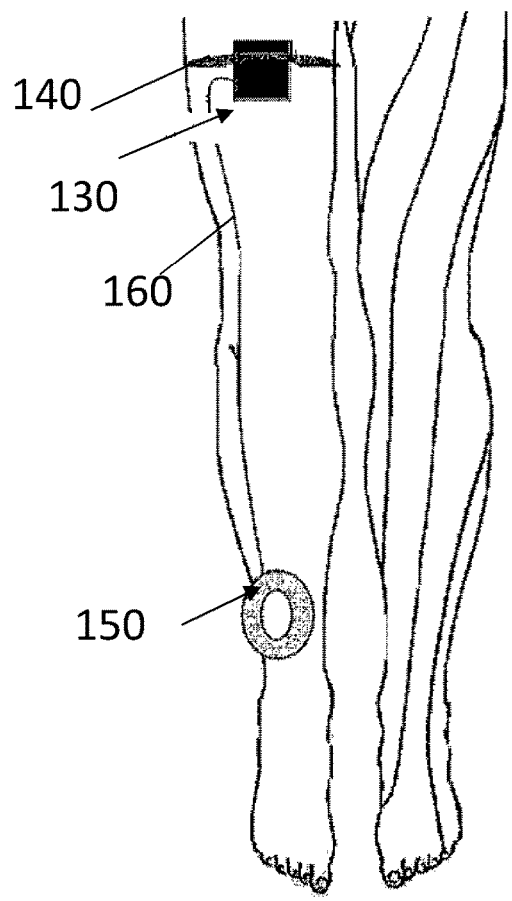
FIG. 15 shows a further application of the embodiment according to FIGS. 10 to 12 in which the flexible element is applied to the leg.

FIGS. 13 to 15 show two application examples of the apparatus described in FIGS. 10 to 12.

130 denotes the control unit and 140 denotes the fastening element by tightening. 150 denotes the flexible support composed of the three layers of the example in FIGS. 10 to 12.

160 denotes the conductors connecting the unit 130 to the electrodes and to the sensors of the flexible support according to FIGS. 10 to 12.

The invention claimed is:

1. An electrical stimulation apparatus, comprising:
    a generator of electrical stimulation pulses, said stimulation pulses being arranged in sequences having predetermined values of typical parameters, said typical parameters comprising amplitude, duration, and frequency of said pulses;
    said generator comprising one or more separate stimulation channels, adapted to deliver said sequences to body areas of an organism in a manner independent for each channel;
    at least one electrode for each stimulation channel, each electrode transmitting the stimulation pulses of a corresponding channel;
    each electrode being applied outside of a patient's skin at a predetermined region and with a predetermined position relation with respect to a position of one or more additional electrodes associated to an additional channel;
    a control unit of said generator, communicating with said generator; and
    an interface for entering setting data and/or commands and for displaying the setting data and/or configuration settings of said generator,
    wherein:
    said at least one electrode or a given number of electrodes are supported by a self-adhesive flexible support element, fastenable in a predetermined position in relation to an anatomy of a human body;
    said at least one electrode or said given number of electrodes being distributed on an extension of said self-adhesive flexible support element according to a predetermined design that is determined by predetermined relations of space positions of said at least one electrode or said electrodes one with respect to each other;
    the generator is connected to the at least one electrode and/or the given number of electrodes provided on the flexible support element, or two or more generators being connected to different electrodes of said given number of electrodes, also supported by said flexible support element,
    said generator or two or more generators are provided with a communication unit for the generator or shared by at least part of each generator, the communication unit being connected to a communication unit of the control unit of said generator or two or more generators, and
    said self-adhesive flexible support further comprises one or more pockets, blisters, or impregnated regions adapted for housing and transdermally administering one or more drugs, said pockets, blisters, or impregnated regions being adjacent to the electrode, or in areas interposed between two or more electrodes, on the same flexible support.

2. The electrical stimulation apparatus according to claim 1, wherein the flexible support element is provided with one or more electrodes and a pulse generator shared by said one or more electrodes, and wherein each electrode is connected to a dedicated independent channel transmitting the stimulation pulses to said electrode.

3. The electrical stimulation apparatus according to claim 1, wherein the control unit that controls said generator is directly associated to the generator and is provided with said generator on a shared support.

4. The electrical stimulation apparatus according to claim 1, wherein the control unit of the generator is separated from the generator and is provided on a further dedicated adhesive flexible support or is borne in a remote position on a garment worn by a user or in a transport bag, carried by the user.

5. The electrical stimulation apparatus according to claim 1, wherein the interface is integrated into or associated with the control unit or is part of a separate and independent device communicating with said control unit or wherein the interface is mounted on a second flexible support or consists of a mobile communication device.

6. The electrical stimulation apparatus according to claim 1, wherein the interface, the control unit and/or the generator has a dedicated power source or a shared power source.

7. The electrical stimulation apparatus according to claim 6, wherein conductors or conductive lines connecting each electrode to an output of the corresponding stimulation channel of the generator are integrated in the flexible support element.

8. The electrical stimulation apparatus according to claim 1, wherein the control unit consists of a mobile communication unit, which executes a control program loaded therein that encodes instructions for a processor and peripheral units of the mobile communication unit to perform functions of the control unit.

9. The electrical stimulation apparatus according to claim 1, wherein the electrical stimulation apparatus has a plurality of electrodes distributed on at least two or more separate flexible supports according to distribution patterns identical or different from one another on at least part of said flexible supports, wherein a generator is provided for each flexible support and comprises a number of channels corresponding to a number of the electrodes present on said flexible support, or a generator shared by all the electrodes of all the flexible supports or at least by a subgroup of the electrodes only of some or all the flexible elements.

10. The electrical stimulation apparatus according to claim 1, wherein each generator has a separate control unit or, as an alternative, the control unit is shared by at least a part of a plurality of generators and at least a further control unit is provided for all or at least part of the remaining generators.

11. The electrical stimulation apparatus according to claim 10, wherein each generator or one generator of each group of generators is directly associated to a dedicated control unit mounted on a same flexible support as the generator or generators.

12. The electrical stimulation apparatus according to claim 10, wherein the control unit of each generator is a remote unit adapted to be mounted on a dedicated flexible support for one or more control units.

13. The electrical stimulation apparatus according to claim 10, wherein the control unit and the interface are mobile communication devices of a user where one or both of a control program or interface program are loaded and executed.

14. The electrical stimulation apparatus according to claim 1, wherein the control unit is directly associated to the interface, or the interface is part of a mobile communication device separate from the control unit.

15. The electrical stimulation apparatus according to claim 1, wherein the at least one electrode or two or more electrodes is shaped as annular or polygonal frames surrounding a central area where there are provided one or more pockets or one or more blisters housing one or more drugs.

16. The electrical stimulation apparatus according to claim 1, wherein the flexible support is prefabricated and has a distribution of electrodes according to a predetermined design, the generator having a number of channels corresponding to a number of the electrodes, and wherein each channel is firmly connected to a corresponding electrode, the generator being configured to control activation and deactivation of each channel regardless of other channels according to activation/deactivation patterns transmitted by the control unit.

17. The electrical stimulation apparatus according to claim 1, wherein a plurality of the electrodes are provided on one face of the flexible support, which is adapted to adhere to the patient's skin, wherein, on an opposite face of the flexible support, a pocket housing one or more generators and/or one or more control units and/or one or more power sources is provided, said pocket being sealed.

18. An electrical stimulation apparatus, comprising:
  a generator of electrical stimulation pulses, said stimulation pulses being arranged in sequences having predetermined values of typical parameters, said typical parameters comprising amplitude, duration, and frequency of said pulses;
  said generator comprising one or more separate stimulation channels, adapted to deliver said sequences to body areas of an organism in a manner independent for each channel;
  at least one electrode for each stimulation channel, each electrode transmitting the stimulation pulses of a corresponding channel;
  each electrode being applied outside of a patient's skin at a predetermined region and with a predetermined position relation with respect to a position of one or more additional electrodes associated to an additional channel;
  a control unit of said generator, communicating with said generator; and
  an interface for entering setting data and/or commands and for displaying the setting data and/or configuration settings of said generator,
  wherein:
  said at least one electrode or a given number of electrodes are supported by a self-adhesive flexible support element, fastenable in a predetermined position in relation to an anatomy of a human body;
  said at least one electrode or said given number of electrodes being distributed on an extension of said self-adhesive flexible support element according to a predetermined design that is determined by predetermined relations of space positions of said at least one electrode or said electrodes one with respect to each other;
  the generator is connected to the at least one electrode and/or the given number of electrodes provided on the flexible support element, or two or more generators being connected to different electrodes of said given number of electrodes, also supported by said flexible support element, and
  said generator or two or more generators are provided with a communication unit for the generator or shared by at least part of each generator, the communication unit being connected to a communication unit of the control unit of said generator or two or more generators, and said self-adhesive flexible support further comprises one or more pockets, blisters, or impregnated regions adapted for housing and transdermally administering one or more drugs, said pockets, blisters, or impregnated regions being adjacent to the electrode, or in areas interposed between two or more electrodes, and wherein the flexible support element comprises:

a first support element for the pockets, blisters, or impregnated regions holding the one or more drugs, a second support element for the one or more electrodes, the first and the second support elements being configured to be fastened to each other, the pockets, the blisters, the first and the second support elements being of toroidal shape and in overlapped relation, the impregnated regions, and the electrodes or blisters being arranged to not overlap one another when the first and the second support elements are coupled, the toroidal shape being shaped to surround an area of interest.

19. The electrical stimulation apparatus according to claim 18, further comprising a third layer covering the first and the second support elements and the area of interest.

20. The electrical stimulation apparatus according to claim 18, wherein the third layer is provided with a zipper so as to enable multiple accesses to the area of interest.

\* \* \* \* \*